United States Patent
Maeva et al.

(10) Patent No.: US 9,743,906 B2
(45) Date of Patent: Aug. 29, 2017

(54) ULTRASONIC DEVICE FOR COSMETOLOGICAL HUMAN NAIL APPLICATIONS

(75) Inventors: Anna Maeva, Windsor (CA); Roman Gr. Maev, Windsor (CA); Liudmila A. Denisova, Windsor (CA)

(73) Assignee: University of Windsor (CA)

( * ) Notice: Subject to any disclaimer, the term of this patent is extended or adjusted under 35 U.S.C. 154(b) by 1069 days.

(21) Appl. No.: 12/131,279

(22) Filed: Jun. 2, 2008

(65) Prior Publication Data

US 2009/0048512 A1  Feb. 19, 2009

Related U.S. Application Data

(60) Provisional application No. 60/941,080, filed on May 31, 2007.

(51) Int. Cl.
*A61B 8/00* (2006.01)
*A61B 8/08* (2006.01)
(Continued)

(52) U.S. Cl.
CPC .......... *A61B 8/0858* (2013.01); *A61B 5/6826* (2013.01); *A61B 5/6838* (2013.01); *A45D 29/00* (2013.01)

(58) Field of Classification Search
None
See application file for complete search history.

(56) References Cited

U.S. PATENT DOCUMENTS 4,341,120 A * 7/1982 Anderson ........................ 73/618
4,385,831 A * 5/1983 Ruell .............................. 356/71

(Continued)

FOREIGN PATENT DOCUMENTS

EP  1297781  4/2003
EP  1298562  4/2003
(Continued)

OTHER PUBLICATIONS

Wollina et al., "Calculation of nail plate and nail matrix parameters by 20 MHz ultrasound in healthy volunteers and patients with skin disease", Skin Research and Technology, 2001; 7:60-64.*
(Continued)

*Primary Examiner* — Jennifer Dieterle
*Assistant Examiner* — Farshad Negarestan
(74) *Attorney, Agent, or Firm* — Carlson, Gaskey & Olds, P.C.

(57) ABSTRACT

An ultrasonic device evaluates the sound velocity of a nail to determine the overall health of a patient and to monitor cosmetological effects of certain products on the nail. The ultrasonic device includes a handhold probe having an piezoelectric transducer encased in cover that emits high-frequency ultrasonic impulses directed towards the nail. The nail reflects returning ultrasonic echoes back to the piezo-electric transducer. The returning ultrasonic echoes vibrate the piezoelectric transducer. A processor of a computer converts the vibrations into electrical pulses. The processor evaluates amplitude values of the electrical pulses to determine the parameters of the human nail, including the thickness, density and elasticity. The parameters are displayed on a display and analyzed by a technician to determine the nail condition. The health of the person or the effect of products on the nail can be determined based on the nail parameters.

4 Claims, 4 Drawing Sheets

(51) Int. Cl.
*A61B 5/00* (2006.01)
*A45D 29/00* (2006.01)

(56) References Cited

U.S. PATENT DOCUMENTS

| | | | |
|---|---|---|---|
| 5,197,475 A * | 3/1993 | Antich et al. | 600/437 |
| 5,224,174 A * | 6/1993 | Schneider et al. | 382/124 |
| 5,284,147 A * | 2/1994 | Hanaoka et al. | 600/462 |
| 5,394,875 A * | 3/1995 | Lewis et al. | 600/445 |
| 5,456,256 A | 10/1995 | Schneider et al. | |
| 5,478,579 A * | 12/1995 | Sawruk | A61K 31/352 424/535 |
| 5,484,586 A | 1/1996 | Bedard | |
| 5,547,988 A * | 8/1996 | Yu | A61K 8/678 514/557 |
| 5,751,835 A * | 5/1998 | Topping et al. | 382/115 |
| 5,918,606 A | 7/1999 | Bilotto | |
| 5,924,427 A | 7/1999 | Jensen | |
| 6,536,065 B2 | 3/2003 | Forrest | |
| 6,546,803 B1 * | 4/2003 | Ptchelintsev et al. | 73/632 |
| 6,631,199 B1 * | 10/2003 | Topping et al. | 382/115 |
| 6,761,697 B2 | 7/2004 | Rubinstenn et al. | |
| 2001/0034009 A1 * | 10/2001 | Lang et al. | 433/173 |
| 2002/0065452 A1 * | 5/2002 | Bazin et al. | 600/300 |
| 2003/0013994 A1 * | 1/2003 | Rubinstenn et al. | 600/587 |
| 2003/0065278 A1 | 4/2003 | Rubinstenn et al. | |
| 2003/0099383 A1 | 5/2003 | Lefebvre | |
| 2005/0154302 A1 | 7/2005 | Sela et al. | |
| 2006/0079780 A1 * | 4/2006 | Karasawa | 600/447 |
| 2007/0037125 A1 * | 2/2007 | Maev et al. | 433/215 |
| 2007/0113655 A1 * | 5/2007 | Reed | 73/606 |
| 2007/0172795 A1 * | 7/2007 | Lang et al. | 433/173 |
| 2007/0197895 A1 * | 8/2007 | Nycz et al. | 600/407 |
| 2007/0232958 A1 * | 10/2007 | Donofrio | A61B 5/0031 600/587 |
| 2010/0227295 A1 * | 9/2010 | Maev et al. | 433/215 |

FOREIGN PATENT DOCUMENTS

| | | |
|---|---|---|
| EP | 1298584 | 4/2003 |
| WO | 95/12354 | 5/1995 |
| WO | 2005/012553 | 2/2005 |

OTHER PUBLICATIONS

Sutton, "Diseases of the skin", St. Louis C. V. Mosby Company, 1917, pp. 857-858.*
Maeva et al. ("Ultrasonic characterization of the biological objects of spherical or cylindrical shape using an acoustic microscope", Acoustical Imaging, vol. 28, pp. 57-64, published on May 19, 2007).*
International Preliminary Report on Patentability for PCT/CA2008/001048 mailed on Dec. 10, 2009.
International Search Report and Written Opinion mailed on Sep. 8, 2008.
Baden, Howard P., "The Physical Properties of Nail," Journal of Investigative Dermatology, vol. 55, No. 2, Aug. 1, 1970, pp. 115-122, XP055053429.
Baden, Howard P. et al., "A Comparative Study of the Physicochemical Properties of Human Keratinized Tissues," BBA—Protein Structure, Elsevier Science BV, Amsterdam, NL, vol. 322, No. 2, Oct. 18, 1973, pp. 269-278, XP024343355.
A.Y. Finlay et al., "Ultrasound transmission time; an in-vivo guide to nail thickness", British Journal of Dermatology, vol. 117, No. 6, Dec. 1, 1987, pp. 765-770, XP002665357.
A.Y. Finlay et al., "Ultrasound velocity in human fingernail and effects of hydration: validation of in vivo nail thickness measurement techniques", British Journal of Dermatology, vol. 123, No. 3, Sep. 1, 1990, pp. 365-373, XP002665358.
H. Zaun, "Brüchige Nägel", Hautarzt, vol. 48, No. 7, Jul. 1, 1997, pp. 455-461, XP002665359.
Extended European Search Report dated Dec. 21, 2011 for EP Application No. 08757184.0.
Maeva A. R., et al.: Ultrasonic Characterization of the Biological Objects of Spherical or Cylindrical Shape Using an Acaustic Microscope, Jan. 1, 2007, Acoustical Imaging, Dordrecht: Springer, 2007, NL, p. 57-64, XP008182713, ISBN: 978-1-4020-5720-5.

* cited by examiner

ULTRASONIC DEVICE FOR COSMETOLOGICAL HUMAN NAIL APPLICATIONS

REFERENCE TO RELATED APPLICATIONS

This application claims priority to U.S. Provisional Application No. 60/941,080 filed May 31, 2007.

BACKGROUND OF THE INVENTION

The invention relates generally to an ultrasonic device that non-invasively and quantitatively evaluates physical properties of a human nail to determine the overall health of a patient.

A condition of a human nail can be an indication of the overall health of a patient. For example, if the nail is soft, brittle or pocked, these symptoms can indicate that the patient may be unhealthy, have a metabolic disorder, a mineral deficiency or a latent disease. Numerous new creams and remedies have been created and used to improve a nail condition. However, there is no reliable and unbiased quantitative method of evaluating the effects of these treatments on the nail.

Nail thickness, density and elasticity are parameters that can reflect the condition of the nail. These nail parameters can indicate the presence of disorders or diseases in a patient and can be used to control and monitor the effectiveness of treatment of general skin and nail diseases. These nail parameters can also be used to control and monitor the positive or negative effects of varnishes, creams and other cosmetics products on the nail.

However, there are no instruments in the clinical and cosmetological practices that can provide a non-invasive quantitative evaluation of nail parameters to allow the nail condition of the patient to be determined.

SUMMARY OF THE INVENTION

An ultrasonic device non-invasively and quantitatively evaluates the sound velocity of a nail to determine various nail parameters, such as the thickness, density and elasticity. The sound velocity is an integral index of the thickness, density and elasticity of the nail.

The nail parameters can be used to indicate a nail condition that reflects a state of the overall health of a patient. The nail parameters can reflect many medical disorders, allowing the health of the patient having a specific medical state to be monitored. The health of the nail itself and the progression and effectiveness of certain nail treatments can also be monitored by measuring the thickness, density and elasticity of the nail.

The ultrasonic device includes a handhold probe including at least one piezoelectric transducer encased in a cover. The handheld probe is positioned over the nail, and the piezoelectric transducer emits high-frequency ultrasonic impulses that are directed towards the nail. The ultrasonic impulses are reflected from an interface between a nail plate and a nail bed of the nail and an upper surface of the nail plate to the piezoelectric transducer as returning ultrasonic echoes that vibrate the piezoelectric transducer.

The ultrasonic device also includes a computer having a processor and a display. The processor converts the vibrations into electrical pulses and evaluates amplitude values of the electrical pulses to determine the thickness, density and elasticity of the nail.

The nail parameters are displayed on the display of the ultrasonic device for evaluation by a technician. Using the nail parameters, the technician can determine the condition of the nail, and therefore the overall health of the person, the relationship to some general diseases, or the effectiveness of a nail treatment.

These and other features of the present invention will be best understood from the following specifications and drawings.

BRIEF DESCRIPTION OF THE DRAWINGS

The various features and advantages of the invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
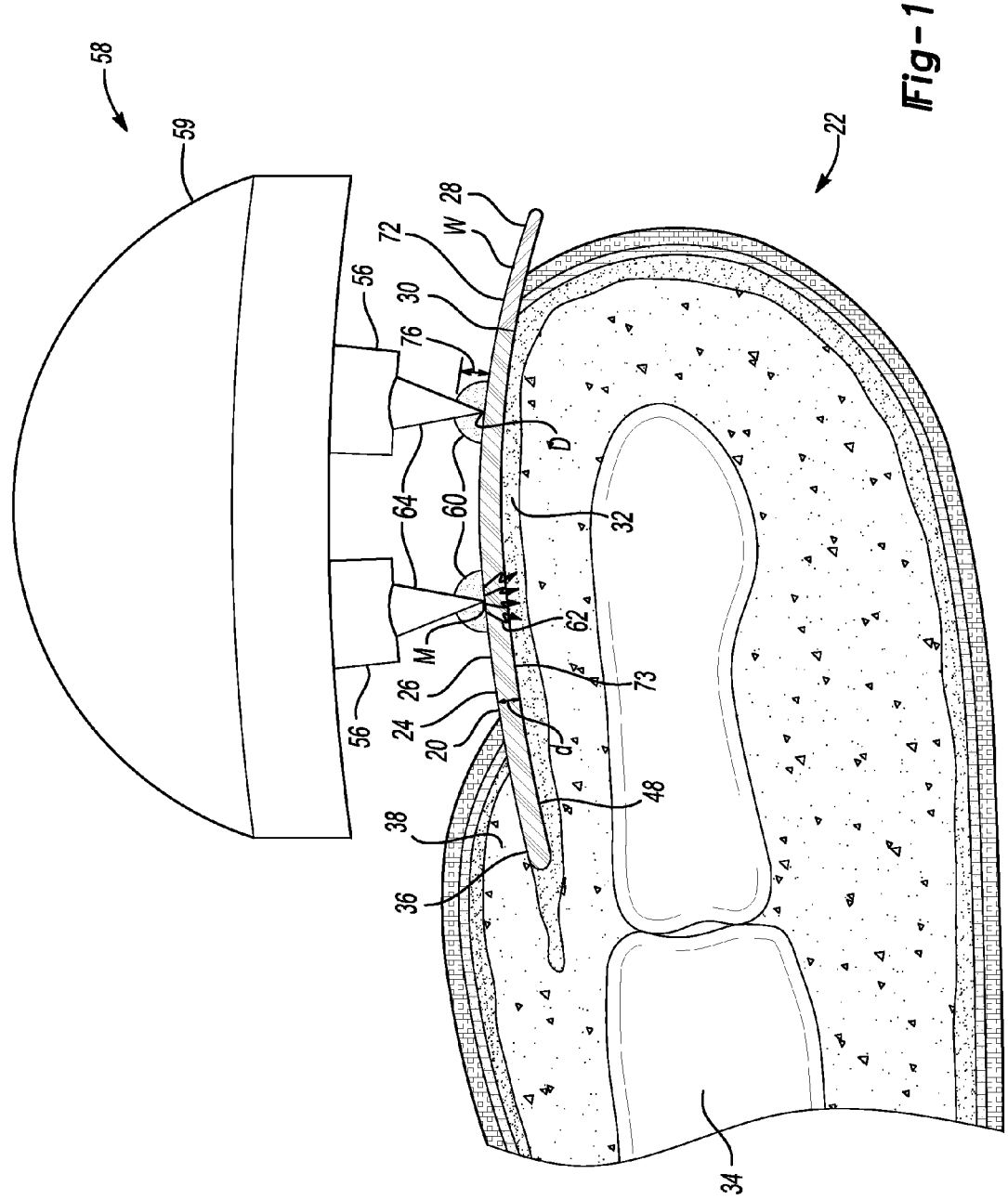
FIG. 1 illustrates a cross-sectional side view of a nail.

FIG. 1 illustrates a nail 20 of a finger or toe 22 of a human. The nail 20 is made of dead cells and keratin and provides protection to sensitive areas of the fingers and toes 22. The nail 20 includes a nail plate 24 having a pink part 26 and a drier white part 28 that meet at an interface 30. The pink part 26 and the white part 28 have approximately the same thickness. The nail plate 24 is located above a soft nail bed 32 with a phalanx bone 34 underneath. The nail bed 32 is the adherent connective tissue located immediately below the nail plate 24 and provides the pinkish color of the nail 20. The nail plate 24 is densely connected with the nail bed 32 at an interface 48. The nail plate 24 grows approximately 100 μm in length a day. A nail root 36 (or nail matrix) is the living part of the fingernail 20 located below a cuticle 38 (eponychium or fold of skin) that protects the nail root 36. Keratin is produced by keratinocytes in the nail root 36.

Sound velocity in the nail plate 24 typically varies between 2100 m/s and 3100 m/s from person to person. The average sound velocity in a person is approximately 2470 m/s. The human nail 20 is not homogeneous in its acoustic properties. For example, sound velocity is lower in the pink part 26 of the nail plate 24, and the sound velocity is up to 30% higher in the white part 28 of the nail plate 24.

Some medical conditions (such as systemic lupus erythematosus, systemic sclerosis, psoriasis, chronic eczema, jaundice and anemia) cause the parameters of the nail 20, such as thickness, density and elasticity, to change. By evaluating and determining the parameters of the nail 20, physicians can monitor the health of patients having the medical conditions described above or determine if the patient has any of these medical conditions. The effects of different nail products can also be tested for safety or the progression of cosmetic nail treatments can be monitored.

Figure 2:
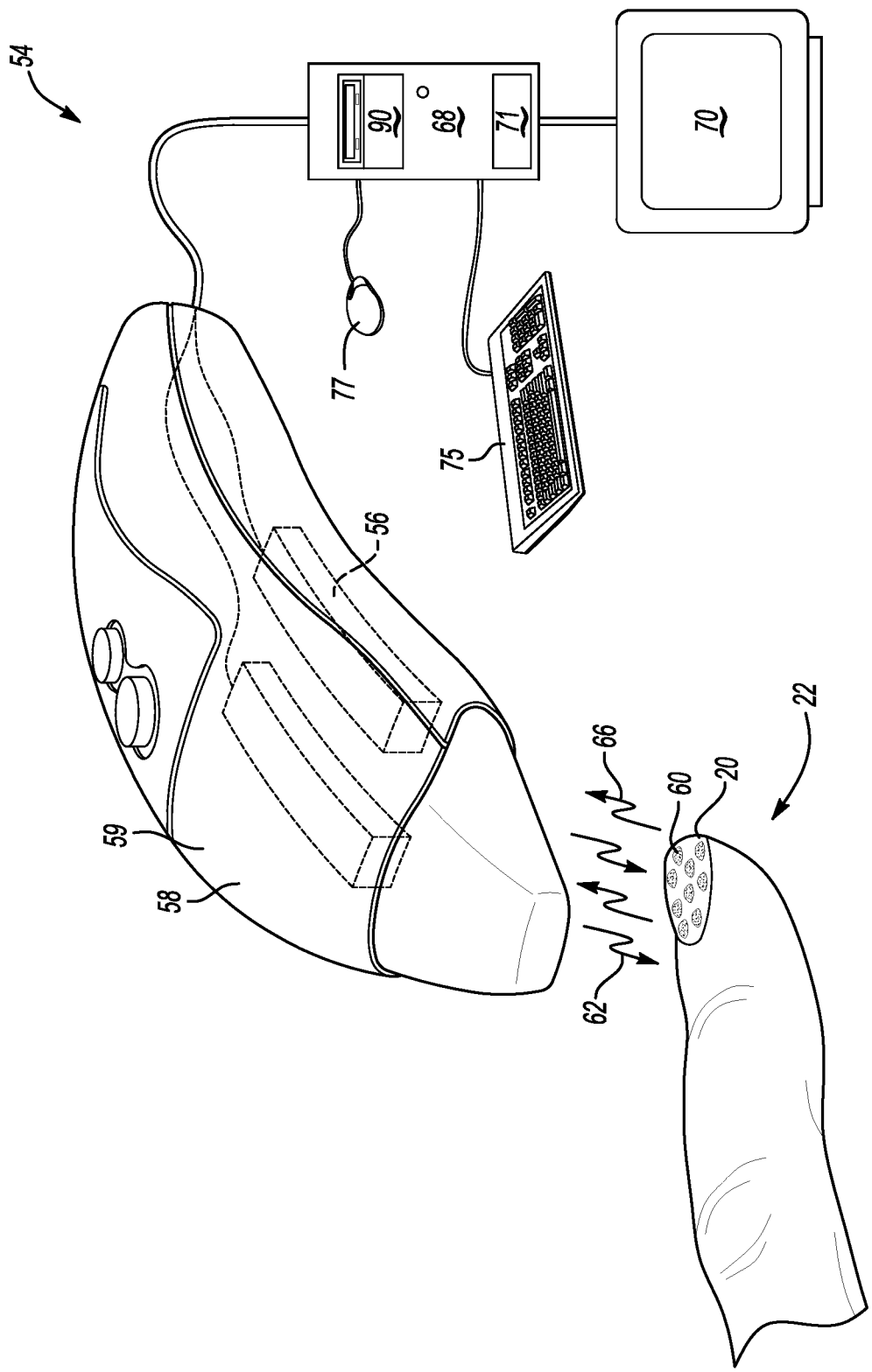
FIG. 2 illustrates an ultrasonic device employed to evaluate the nail.
Figure 3:
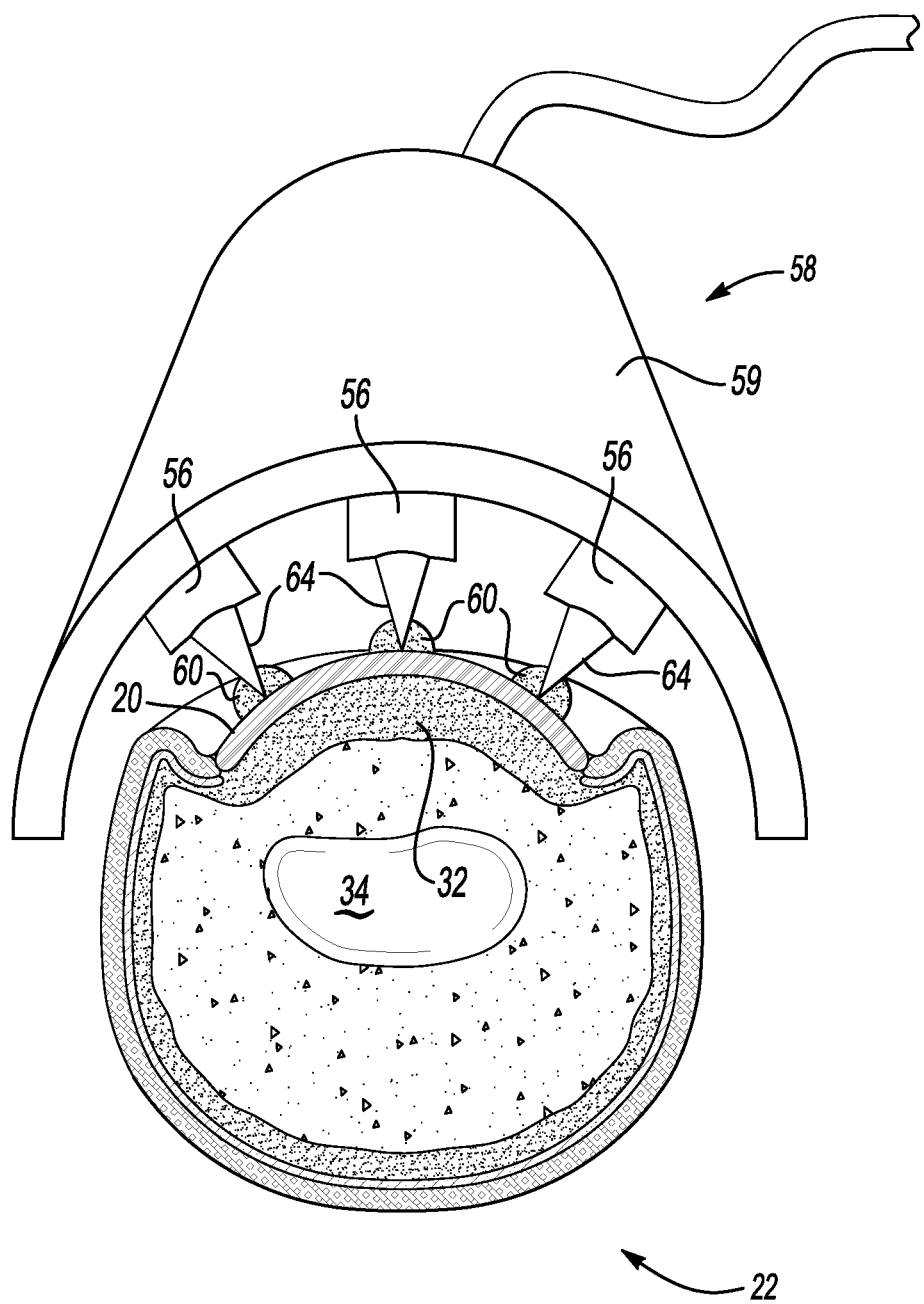
FIG. 3 illustrates a top view of the nail.

FIGS. 2 and 3 show an ultrasonic device 54 that safely and non-invasively quantifies and evaluates the nail 20 in vivo. The ultrasonic device 54 includes a handheld probe 58 that generates an ultrasonic signal. The handhold probe 58 includes including a cover 59 that encases at least one piezoelectric transducer 56. The piezoelectric transducer 56 generates high-frequency ultrasonic impulses 62 (sound waves), and the cover 59 directs the ultrasonic impulses non-invasively towards the nail 20. The cover 59 can encase more than one piezoelectric transducer 56 to provide simultaneous measurements in several points on the surface of the nail plate 24. In one example, the ultrasonic device 54 is portable and handheld. An example ultrasonic device 54 is the ultrasonic device "Tessonics-AM 1163". However, it is to be understood that different types of ultrasonic device 54 can be employed.

Different transducers 56 may be employed and switched on as desired to investigate different properties of the nail 20. Different sets of transducers 56 can be used (in a set of two) to allow two readings to be taken simultaneously from two different location on the nail 20.

The ultrasonic device 54 also includes a computer 68 having a storage 90 (memory, hard drive, optical and/or magnetic, etc.) and a processor 71 (or CPU) that provides a quantitative analysis of the nail 20. The ultrasonic device 54 also includes a keyboard 75, a mouse 77 and a display 70 that displays data and images.

A coupling media 60 (such as a water-based gel) is applied on an upper surface 72 of the nail plate 24. The handheld probe 58 positioned over the nail 20 directs the ultrasonic impulses 62 towards the nail 20. The handheld probe 58 is provided with a PVC-conical delay 64 that is coupled directly on the nail plate 24, but there is some distance 76 between the upper surface 72 of the nail 20 and the edge of the conical delay 64 where the coupling media 60 is located. In one example, the ultrasonic device 54 is operated with a frequency 15 MHz. Frequencies in the range of 15-75 MHz can be also employed.

The ultrasonic impulses 62 contact the nail 20 and reflect off the upper surface 72 of the nail plate 24 and the interface 48 between the nail plate 24 and the nail bed 32 as returning ultrasonic echoes 66. The returning ultrasonic echoes 66 vibrate the piezoelectric transducer 56. The processor 71 converts the vibrations into electrical pulses. The electrical pulses represent evaluative data that is representative of the parameters of the nail 20 (including thickness, density and elasticity) which are calculated as described below.

Images and data representing the electrical impulses are shown on the display 70. The processor 71 processes amplitude values of the electrical impulses to determine the parameters of the nail 20. The parameters processed by the processor 71 are also displayed on the display 70. For example, a numerical value representing each of the thickness, density and elasticity of the nail 20 can be displayed on the display 70. A technician can evaluate the nail parameters displayed on the display 70 to determine if a patient has a medical condition or can keep track of the progress of a cosmetological treatment.

Returning to FIG. 1, ultrasound time-of-flight (TOF) is the time interval between the ultrasonic beam reflecting off the upper surface 72 of the nail plate 24 and the interface 48 between the nail plate 24 and the nail bed 32.

Figure 4:
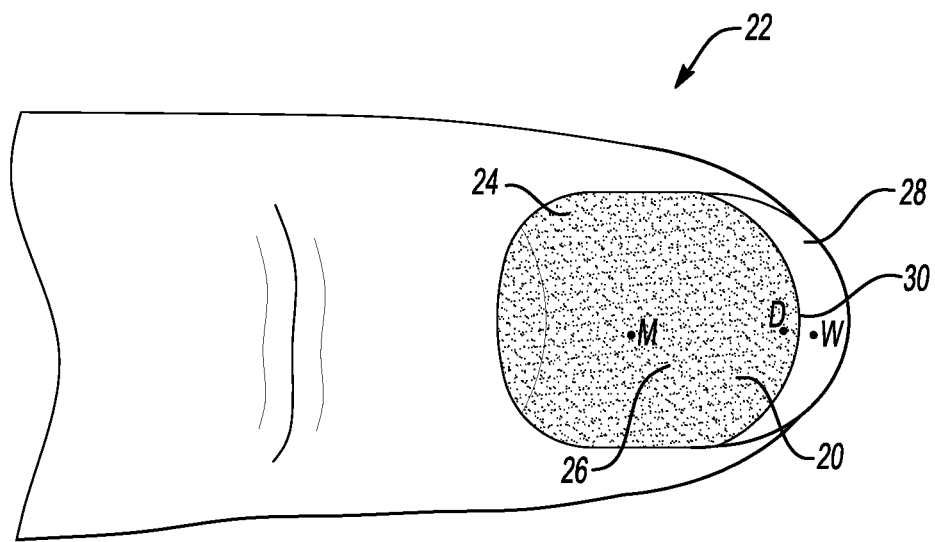
FIG. 4 illustrates an end view of the nail.

As shown in FIG. 4, the time-of-flight of the ultrasound signal is determined at least two points of the nail 20: 1) at a central area M of the pink part 26 and 2) at a middle D of a distal edge of the pink part 26 near the interface 30 between the pink part 26 and the white part 28. The time-of-flight between the transmission of the ultrasonic impulse 62 and the returning ultrasonic echoes 66 to the handheld probe 58 is used to calculate the depth of the tissue interface 48 and the thickness of the nail 20. The greater the amount of time it takes for the returning ultrasonic echoes 66 to return to the handheld probe 58, the greater the distance between the nail plate 24 and the nail bed 32 and/or the greater the sound velocity in the nail plate 24.

The ultrasonic device 54 can be used to determine the thickness of the nail 20. To determine the thickness of the nail 20, a thickness $d_W$ of the nail plate 24 in the middle of the white part 28 is measured with a caliper at a point W that is as close to a boundary with the pink part 26 as possible. The thickness $d_W$ at the point W is inputted into the computer 68 using the keyboard 75. The thickness $d_W$ is approximately equal to a thickness $d_D$ at a point that is at a middle of D a distal edge of the pink part 26.

The thickness $d_D$ can be used to calculate the longitudinal ultrasound velocity $C_D$ at the middle D of the nail plate 24 using the formula:

$$C_D = TOF_D / 2d_D \quad \text{(Equation 1)}$$

where $TOF_D$ is the time-of-flight at the point D as measured by the ultrasonic device 54.

The deviations of longitudinal ultrasound velocity at a point M in a central area of the pink part 26 does not usually exceed 3-5%. The longitudinal ultrasound velocity $C_D$ at the point D calculated using Equation 1 can be used to calculate the thickness $d_M$ of the nail plate 24 at the point M using the formula:

$$d_M = (C_D \times TOF_M)/2 \quad \text{(Equation 2)}$$

where $TOF_M$ is the time-of-flight at the point M as measured by the ultrasonic device 54. The thickness $d_M$ at the point M of the nail 20 can be calculated using time-of-flight as detected by the ultrasonic device 54 at different locations of the nail 20. Therefore, the thickness of the nail 20 at different locations can be calculated by the computer 68 and displayed on the display 70 for evaluation by a technician.

The ultrasonic device 54 can also be used to calculate the density and the elasticity of the nail 20. The longitudinal ultrasound velocity C (calculated in Equation 1) correlates with the density and the elasticity of the nail 20. The longitudinal ultrasound velocity C can be defined using the following formula:

$$C^2 = E/\rho \quad \text{(Equation 3)}$$

where E is the elasticity of the nail 20, and $\rho$ is the density of the nail 20.

The amplitude value of the ultrasound signal changes while the ultrasonic impulse 62 travels inside the nail plate 24 due to the sound energy attenuation. By measuring the local values of the intensity of the ultrasonic impulses 32 and the returning ultrasonic echoes 66 reflected from the interface 48 between the nail plate 24 and nail bed 32 and the time-of-flight, the local values of density and elasticity can be determined.

A coefficient of reflection R and a coefficient of transmission T of acoustic pressure when acoustic waves fall perpendicularly on a boundary from media 1 to media 2 is defined as $$R = \frac{z_2 - z_1}{z_2 + z_1} \text{ and } T = \frac{2z_2}{z_2 + z_1} \quad \text{(Equation 4)}$$

The amplitudes $A_1$ and $A_2$ of the impulses reflected from an upper surface 72 and a lower surface 73 of the nail plate 24, respectively, can be defined by:

$$A_1 = A_0 \frac{z_n - z_g}{z_n + z_g} \varepsilon_{gn} \quad \text{(Equation 5)}$$

-continued $$A_2 = A_0 \left(\frac{2z_n}{z_n + z_g}\varepsilon_{gn}\right)\left(\frac{z_t - z_n}{z_n + z_t}\varepsilon_{nt}\right)\left(\frac{2z_g}{z_n + z_g}\varepsilon_{gn}\right)e^{-\alpha \cdot 2d} \quad \text{(Equation 6)}$$

where $z_n$, $z_t$ and $z_g$ are the acoustic impedances of the nail 20, the nail bed 32 and the coupling media 60, respectively, $\varepsilon_{gn}$ and $\varepsilon_{nt}$ are the empirical coefficients which introduce the effect of sound losses at the boundary between the coupling media and nail and the nail/nail bed, respectively, due to the small irregularities on the boundary,
α is the attenuation coefficient of the nail 20, and
d is the thickness of the nail 20.

Using Equations 5 and 6, the ratio ($K_1$) of the amplitudes $A_2$ to $A_1$ is defined as:

$$k_1 = \frac{A_2}{A_1} = \frac{4z_g z_n (z_t - z_n)}{(z_n^2 - z_g^2)(z_t + z_n)}(\varepsilon_{gn})(\varepsilon_{nt})e^{-\alpha \cdot 2d} \quad \text{(Equation 7)}$$

At the contact area between the piezoelectric transducer 56 and the nail 20, the radius of curvature of the nail 20 is much larger than a width of the contact area. However, the large-scale curvature of the nail 20 does not play a significant role near the contact area. Therefore, the effect of large-scale curvature on the sound propagation can be neglected. Sound losses due to the small-scale unevenness are small.

The empirical coefficients $\varepsilon_{gn}$ and $\varepsilon_{nt}$ are approximately ≈1. The attenuation in the nail 20 is small (α≈0). Impedances of the coupling media (gel or water) $z_g$ are 1.5 MRayl, and the impedance of the nail bed $z_t$ is 1.6 MRayl (a typical value for the most of soft tissue).

Under such assumptions, the ratio $k_1$ depends only on the unknown impedance of the nail $z_n$. Equation 7 can then be solved for the acoustic impedance of the nail $z_n$.

The ratio $k_1$ can be measured from A-scans of nail 20 (voltage readings in the device used are proportional to the acoustic pressure). As determined above, the impedance of the nail $z_n$ can be calculated and the measured value of $k_1$. The density of the nail 20 can be defined as:

$$\rho = z_n/C \quad \text{(Equation 8)}$$

Solving for C, $$C = z_n/\rho \quad \text{(Equation 9)}$$

Solving Equation 3 for the elasticity E, $$E = \rho \cdot C^2 \quad \text{(Equation 10)}$$

Adding the value of ρ from Equation 8, E can be defined as:

$$E = z_n \cdot C \quad \text{(Equation 11)}$$

The longitudinal ultrasound velocity C can be determined using time-of-flight as detected by the ultrasonic device 54 in different locations of the nail 20 using Equation 1 as described above. Once the impedance of the nail $Z_n$ is known, density ρ can be determined using Equation 8. The elasticity E can be determined using Equation 11.

After the thickness d, the elasticity E, and the density ρ of the nail 20 are calculated by the computer 68 and determined using the above equations, these values are displayed on the display 70. A technician evaluates these parameters to evaluate the condition of the nail 20. For example, the values or parameters can be shown as numbers on the display 70. Once a technician evaluates the parameters, the technician can determine a condition of the nail and the health of the patient or the effect of nail treatments on a nail by comparing the values calculated by the ultrasonic device 54 with known values.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A method for evaluating a nail, the method comprising the steps of:
    generating an ultrasonic wave with an ultrasonic source;
    transmitting the ultrasonic wave towards the nail with the ultrasonic source;
    receiving returning ultrasonic echoes reflected from the nail;
    analyzing the returning ultrasonic echoes to determine a thickness, density, and elasticity of the nail with a computer;
    comparing the determined thickness, density, and elasticity of the nail to known values; and
    determining a condition of the nail based on the step of comparing to determine if a patient has a disease.

2. The method as recited in claim 1 wherein the ultrasonic wave has a frequency between 15 MHz and 50 MHz.

3. The method as recited in claim 1 wherein the determined thickness, density, and elasticity are indicative of a medical condition of a patient.

4. The method as recited in claim 1 including the step of displaying data representative of the determined thickness, density, and elasticity of the nail on a display.

* * * * *